(12) United States Patent
Buza et al.

(10) Patent No.: US 11,134,963 B2
(45) Date of Patent: Oct. 5, 2021

(54) PATIENT-SPECIFIC CUTTING GUIDE FOR THE SHOULDER

(71) Applicant: Howmedica Osteonics Corp., Mahwah, NJ (US)

(72) Inventors: Luke Buza, Flemington, NJ (US); Gennaro A. Barile, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 982 days.

(21) Appl. No.: 15/055,109

(22) Filed: Feb. 26, 2016

(65) Prior Publication Data

US 2016/0174993 A1 Jun. 23, 2016

Related U.S. Application Data

(63) Continuation of application No. 14/124,422, filed as application No. PCT/US2012/040831 on Jun. 5, 2012, now Pat. No. 9,301,768.

(Continued)

(51) Int. Cl.
*A61B 17/16* (2006.01)
*A61B 17/15* (2006.01)
(Continued)

(52) U.S. Cl.
CPC .......... *A61B 17/1684* (2013.01); *A61B 17/15* (2013.01); *A61B 17/1778* (2016.11);
(Continued)

(58) Field of Classification Search
CPC ............ A61B 17/1684; A61B 17/1778; A61B 17/1664; A61B 17/1666; A61B 17/1668;
(Continued)

(56) References Cited

U.S. PATENT DOCUMENTS

| 5,800,551 A | 9/1998 | Williamson et al. |
| 6,129,764 A | 10/2000 | Servidio |

(Continued)

OTHER PUBLICATIONS

Partial ISR dated Aug. 31, 2012 for PCT/US2012/040831.

(Continued)

*Primary Examiner* — Si Ming Ku
(74) *Attorney, Agent, or Firm* — Lerner, David, Littenberg, Krumholz & Mentlik, LLP

(57) ABSTRACT

Disclosed herein are patient-specific cutting guides for guiding a surgical instrument for resecting a portion of a glenoid of a patient. The cutting guides include a base portion having a contact surface shaped to substantially match at least a portion of a cavity of the glenoid. The base portion has a guide hole extending therethrough in which the guide hole has an axis coaxial with an axis of rotation. The cutting guides include one or more stabilization members extending outwardly from the base portion and having a contact surface shaped to substantially match an outer surface of a portion of a scapula of the patient. The stabilization members are oriented to take into account the patient's anatomy in orienting and stabilizing the guide with respect to the glenoid. The guide hole of the base portion is for guiding the surgical instrument to create a guide hole in the glenoid.

18 Claims, 9 Drawing Sheets

Related U.S. Application Data

(60) Provisional application No. 61/494,579, filed on Jun. 8, 2011.

(51) Int. Cl.
  *A61B 17/17* (2006.01)
  *G16H 50/50* (2018.01)
  *A61B 34/10* (2016.01)
  *A61B 90/00* (2016.01)

(52) U.S. Cl.
  CPC ........ G16H 50/50 (2018.01); *A61B 2034/108* (2016.02); *A61B 2090/033* (2016.02); *Y10T 29/49* (2015.01)

(58) Field of Classification Search
  CPC . A61B 17/1742; A61B 17/1746; A61B 17/15; A61B 17/16
  USPC .......................................................... 606/87
  See application file for complete search history.

(56) References Cited

U.S. PATENT DOCUMENTS

| | | | |
|---|---|---|---|
| 6,364,910 | B1 | 4/2002 | Shultz et al. |
| 7,070,662 | B2 | 7/2006 | Studebaker |
| 7,537,618 | B2 | 5/2009 | Collazo |
| 7,604,665 | B2 | 10/2009 | Iannotti et al. |
| 7,785,370 | B2 | 8/2010 | Collazo |
| 7,785,371 | B2 | 8/2010 | Collazo |
| 2004/0030245 | A1 | 2/2004 | Noble et al. |
| 2005/0148843 | A1 | 7/2005 | Roose |
| 2005/0245808 | A1 | 11/2005 | Carson |
| 2006/0004373 | A1 | 1/2006 | Ondrla et al. |
| 2006/0136058 | A1 | 6/2006 | Pietrzak |
| 2008/0161815 | A1 | 7/2008 | Schoenefeld et al. |
| 2008/0257954 | A1 | 10/2008 | Naccache et al. |
| 2009/0110498 | A1 | 4/2009 | Park |
| 2009/0157083 | A1 | 6/2009 | Park et al. |
| 2010/0023015 | A1 | 1/2010 | Park |
| 2010/0076563 | A1 | 3/2010 | Otto et al. |
| 2010/0153081 | A1 | 6/2010 | Bellettre et al. |
| 2010/0217270 | A1 | 8/2010 | Polinski et al. |
| 2010/0305574 | A1 | 12/2010 | Fitz et al. |
| 2010/0312160 | A1 | 12/2010 | Creighton et al. |
| 2011/0015639 | A1 | 1/2011 | Metzger et al. |
| 2011/0029088 | A1 | 2/2011 | Rauscher et al. |
| 2011/0054478 | A1 | 3/2011 | Vanasse et al. |
| 2011/0130795 | A1 | 6/2011 | Ball |
| 2011/0190775 | A1* | 8/2011 | Ure ............... A61F 2/4609 606/91 |
| 2012/0078258 | A1 | 3/2012 | Lo et al. |
| 2012/0078259 | A1* | 3/2012 | Meridew ............ A61F 2/34 606/87 |
| 2012/0141034 | A1 | 6/2012 | Iannotti et al. |
| 2012/0143267 | A1* | 6/2012 | Iannotti ............ A61B 34/10 606/86 R |

OTHER PUBLICATIONS

International Search Report and Written Opinion for Application No. PCT/US2012/040831 dated Dec. 11, 2012.
U.S. Appl. No. 12/541,443, filed Aug. 14, 2009.

\* cited by examiner

PATIENT-SPECIFIC CUTTING GUIDE FOR THE SHOULDER

CROSS-REFERENCE TO RELATED APPLICATIONS

This application is a continuation of U.S. application Ser. No. 14/124,422, filed on Jan. 29, 2014, which claims the benefit of national phase entry under 35 U.S.C. § 371 of International Application No. PCT/US2012/040831 filed Jun. 5, 2012, published in English, which claims the benefit of the filing date of U.S. Provisional Application No. 61/494,579, filed Jun. 8, 2011, entitled, "Patient-Specific Cutting Guide For The Shoulder," the disclosures of which are hereby incorporated herein by reference.

FIELD OF THE INVENTION

The present invention relates to patient-specific cutting guides for the shoulder, and in particular it relates to such cutting guides having a patient-specific contact surface shaped to rest on bone in a predetermined manner, the guides having at least one guide hole or slot used to resect bone as preoperatively planned such that a corresponding implant can be located and oriented on the resected bone in a predefined manner.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in the case where tendons in a joint become lax or soft tissues in or adjacent the joint tear become damaged or worn.

Arthroplasty procedures can be used to repair damaged joints. During a typical arthroplasty procedure, an arthritic or otherwise dysfunctional joint can be remodeled or realigned, or an implant or implants can be implanted into the damaged region. Arthroplasty procedures may take place in any of a number of different regions of the body, such as a knee, a hip, a shoulder, or an elbow.

One type of arthroplasty procedure is a shoulder arthroplasty, in which a damaged shoulder joint is replaced with prosthetic implants. The shoulder joint may have been damaged by, for example, arthritis (e.g., severe osteoarthritis or degenerative arthritis), trauma, or a rare destructive joint disease.

Implants that are implanted into a damaged region may provide support and structure to the damaged region, and may help to restore the damaged region, thereby enhancing its functionality. Prior to implantation of an implant in a damaged region, the damaged region may be prepared to receive the implant. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation may be used for locating a position and orientation to resect the humeral head for proper humeral stem placement in the humerus.

Accuracy in implant alignment is an important factor to the success of the procedure. A one to two millimeter translational misalignment, or a one to two degree rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. Currently available instrument and tools do not always enable the surgeon to make the most accurate cuts on the bone surface in preparing the target joint for implantation. Thus, there remains a need for tools that improve the accuracy of the joint resurfacing process.

BRIEF SUMMARY OF THE INVENTION

Patient-specific cutting guides for resecting the humerus and glenoid in a preoperatively planned manner are described herein. These patient-specific guides are configured to allow a surgeon to accurately and quickly perform a shoulder arthroplasty procedure that substantially restores the natural alignment of the joint. Specifically, the patient-specific guides are shaped such that they matingly receive the regions of the bone to be subjected to a treatment (e.g., cutting, drilling, reaming, and/or resurfacing). The patient-specific guides are also shaped to provide the proper location and orientation of the treatment relative to the regions of the bone. The shaped aspect of the patient-specific guides allows the treatment of the bone regions to be done quickly and with a high degree of accuracy that will allow the implants to restore the patient's joint to a generally pre-deteriorated state.

The disclosed guides relate to a prosthetic device system for repairing ball-and-socket type joints in a human body, particular shoulder joints. Applicants incorporate by reference in its entirety herein the disclosure of U.S. Pat. No. 7,537,618 ("the '618 Patent"), which relates to a modular anatomic adjustable prosthetic device system for the shoulder and hip joints. U.S. Pat. Nos. 7,785,370 and 7,785,371 which claim priority to the '618 Patent, the disclosures of which are also incorporated by reference in their entirety herein.

DETAILED DESCRIPTION

Figure 1:
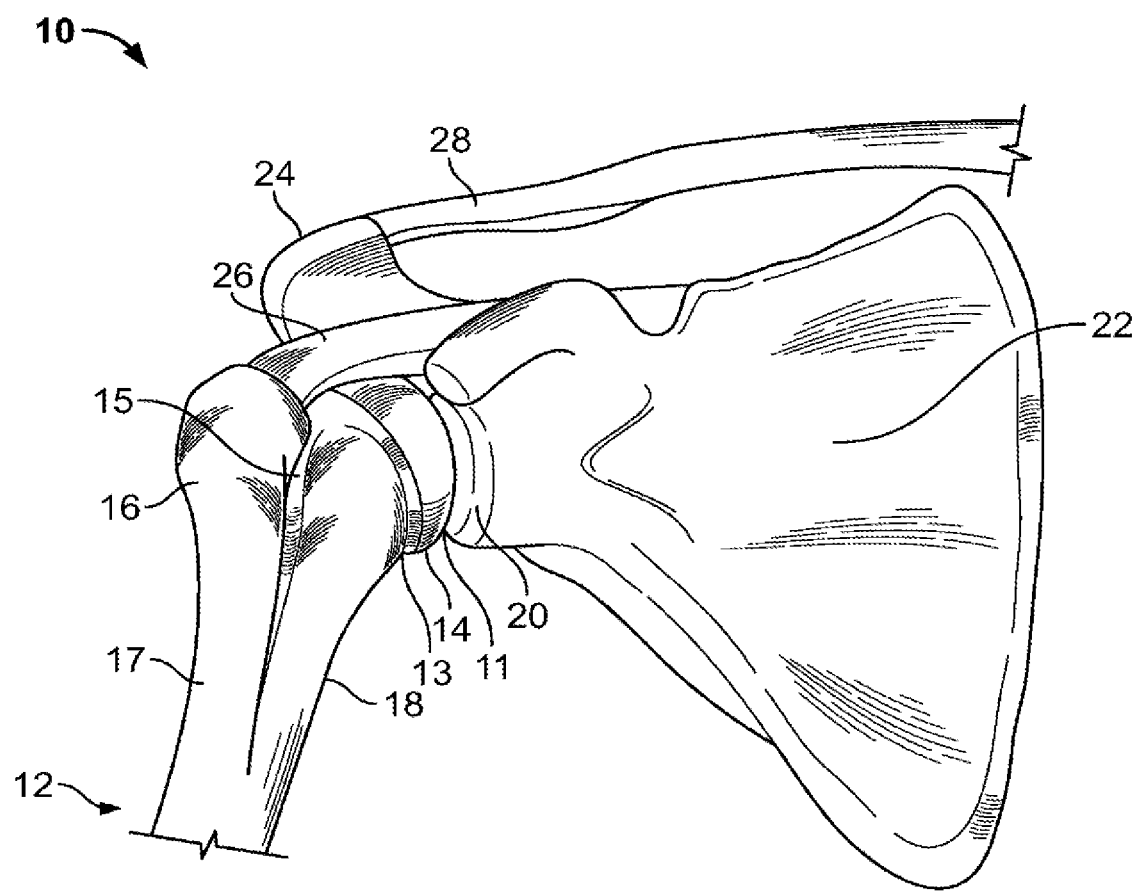
FIG. 1 shows the general shoulder joint anatomy of a patient.
Figure 2:
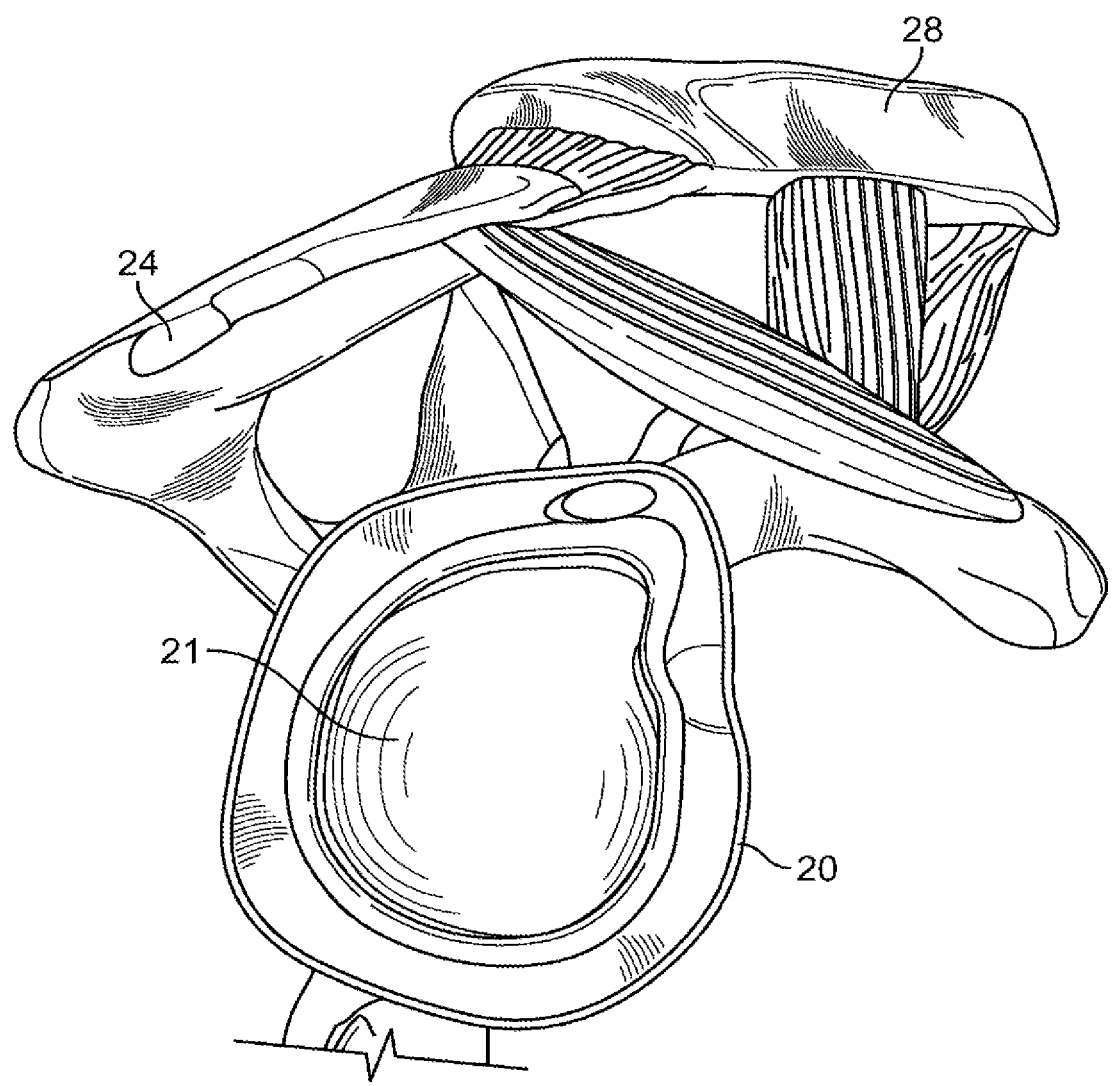
FIG. 2 is a view of a glenoid cavity of the shoulder joint.

FIG. 1 shows the general anatomy of shoulder joint 10 of a patient. Humerus 12 of joint 10 includes a neck portion 13, a head portion 14 and a shaft portion 17 having a greater tuberosity 16 and a lesser tuberosity 18. Between greater and lesser tuberosities 16, 18 is bicipital groove 15. As shown in FIGS. 1-2, scapula 22 terminates at glenoid 20 having a cavity 21 in which an outer surface 11 of head portion 14 rotates within. Along with humerus 12 and scapula 22, the acromion 24, rotator cuff 26 and clavicle 28 all provide support to the range of motion of the shoulder joint 10 of the patient.

Figure 3:
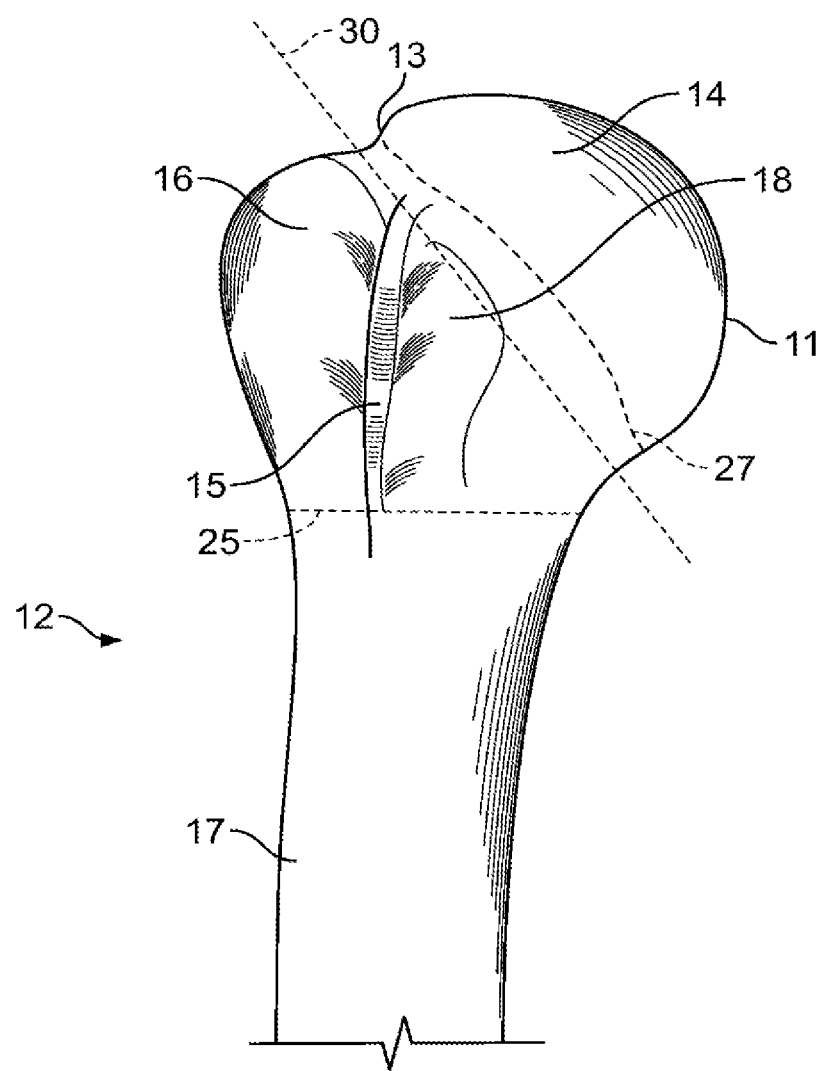
FIG. 3 is a posterior view of a proximal portion of a humerus of the shoulder joint showing a resection line adjacent the anatomical neck of a humerus, the resection line corresponding to the preoperatively planned location and orientation of a humeral stem component that will be implanted in a shoulder arthroplasty procedure.
Figure 4:
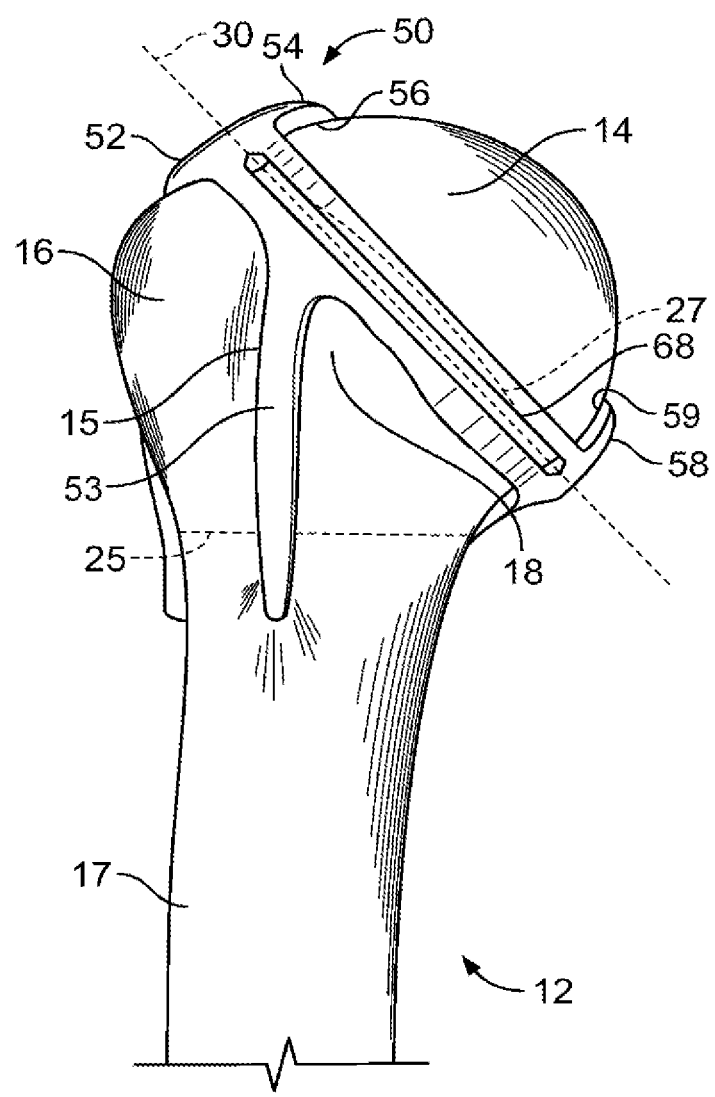
FIG. 4 is a view of an embodiment of a patient-specific cutting guide of the present invention for resecting the humerus.

FIG. 3 is a posterior view of a proximal portion of humerus 12 of shoulder joint 10. Head portion 14 includes outer surface 11. Also shown is bicipital groove 15, a substantially straight surcical neck line 25 and a curvy anatomical neck line 27. Outer surface 11, bicptal groove 15, substantially straight surcical neck line 25 and curvy anatomical neck line 27 are all anatomical features of humerus 12 that can be used to aid in the designing of one or more patient-specific contact surfaces that may be located a guide 50, for example, as shown in FIG. 4, and thereafter accurately locate guide 50 on humerus 12.

Prior to a total shoulder arthroplasty procedure being conducted, shoulder joint 10 is generally compromised through injury or general wear and tear. A compromised joint generally leads to range of motion difficulty and pain for the patient. In a joint 10 that is compromised, head portion 14 and/or glenoid cavity 21 may be degenerated such that the axis of rotation of the shoulder joint is not in the same location as it was prior to joint 10 being compromised.

The axis of rotation of the shoulder joint varies based upon the type of motion. For flexion and extension, the axis of rotation is a transverse axis though the center of the humeral head. For abduction and adduction, the axis of rotation is a sagittal axis thought the center of the humeral head. For internal and external rotation, the axis of rotation is a vertical axis though the center of the humeral head.

During a total shoulder arthroplasty procedure, the humerus is resected in order to receive a humeral stem component. In such a procedure, the humeral head is generally resected and the shaft of the humerus is reamed to receive the humeral stem component prosthesis. It is important that the humeral stem component be positioned in the correct location and orientation in order to restore the axis of rotation of joint 10. Some humeral stem components may include a flange that is adapted to contact a flat portion of resected bone of the humerus in order to correctly position and stabilize the humeral stem component within shaft 17 of humerus 12 such that the axis of rotation of joint 10 may be restored.

Also during a total shoulder arthroplasty procedure, the glenoid is resected in order to receive a glenoid component. In a shoulder arthroplasty procedure for implanting a reverse shoulder prosthesis, a cavity of the glenoid may be reamed and a guide hole may be drilled in order to receive a central screw extending outwardly from an outer contact surface of the glenoid component. The location and orientation of the guide hole may be based on the shape of the glenoid component, for example, such that the glenoid component can be implanted in the resected glenoid cavity and the axis of rotation of the joint may be restored. It is important that the glenoid component be positioned in the correct location and orientation in order to restore the axis of rotation of joint 10. The glenoid component preferably has an articular surface corresponding to an outer surface of a humeral head component which is engaged to the humeral stem component implanted at least partially within the shaft of the humerus. Generally, the glenoid component has a diameter that is approximately 6 mm in diameter larger than the humeral stem component.

As discussed above, humerus 12 must be resected at the correct location and orientation in order for a corresponding humeral stem prosthesis to be accurately implanted in shaft 17 of humerus 12 such that the axis of rotation of the shoulder joint may be restored. Thus, the location and orientation of resection line 30, as shown in FIG. 3, is preoperatively planned according to one aspect of the present invention. Resection line 30 corresponds to the location and orientation of resection slot 68 of guide 50, as shown in FIG. 4, once located and oriented on neck portion 11 and head portion 14 of humerus 12.

In order to preoperatively plan the location and orientation of slot 68 of guide 50, joint 12 first has to be scanned. After joint 10 is scanned using CT or MRI, for example, the images obtained from the scan are used to create a 3D model (not shown) of the shoulder joint. A technician preferably then selects certain points on the 3D model that the patient-specific cutting guide will contact with contact surfaces that match at least a portion of the area of the humerus surrounding the selected points. For instance, the technician may select points located on neck portion 13 of humerus and attach the points with splines. Once a line is created on neck portion 13, a patient-specific contact surface (not shown) on guide 50 is preferably created to substantially match the contour of the line such that guide 50, once manufactured, will contact the actual outer surface of humerus 12 in a predetermined location and orientation while being substantially stabilized thereto. Patient-specific cutting guide 50, as shown in FIG. 4, can be manufactured via SLA, milled from a jig blank, or molded, for example.

FIG. 4 shows patient-specific cutting guide 50 for guiding a surgical instrument, such as a saw blade (not shown) for resecting a portion of humerus 12. Guide 50 includes a base portion 52 having a contact surface shaped to substantially match an outer surface of a neck portion 13 of humerus 12. Guide 50 further includes at least one proximal stabilization member 54 extending medially from base portion 52 and having a contact surface 56 shaped to substantially match an outer surface 11 of a head portion 14 of humerus 12. Preferably, guide 50 also includes at least one distal stabilization member 53 extending distally from base portion 52 and having a contact surface shaped to substantially match an outer surface of a shaft portion 17 of humerus 12.

A generally reproducible feature on the humerus is bicipital groove 15, which contains the long head of the biceps tendon. The contact surface of the distal stabilization member 53 is shaped to match a location on the bicipital groove 15 of humerus 12. Another generally reproducible feature on the humerus is anatomic neck 27. The contact surface of base portion 52 of guide 50 is shaped to match a location either on or adjacent to anatomic neck line 27 of humerus 12.

Preferably, guide 50 contacts bone on humerus 12 in at least three locations in order to substantially stabilize guide 50 when it is being used to resect humerus 12. Proximal stabilization member 54 as well as proximal stabilization member 58 having patient-specific contact surface 59 are preferably used in conjunction with distal stabilization member 53 in order to stabilize guide 50 sufficiently on humerus 12.

Guide 50 may also be pinned in place by placing pins through pin holes (not shown) in guide 50 preferably at some point along base portion 52. Preferably, base portion 52 of guide 50 includes two guide holes adapted to receive a stabilization pin therein for securing guide 50 to humerus 12. In one embodiment, guide 50 includes a first guide hole located on base portion 52 superior to guide slot 68 and a second guide hole located on base portion 52 anterior to guide slot 68.

Figure 5:
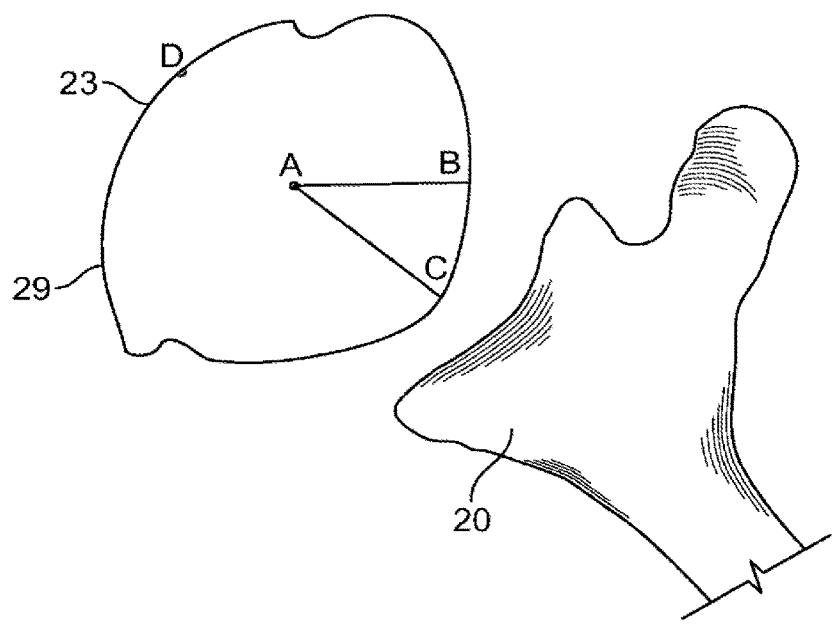
FIG. 5 is a top view of a humerus stem and glenoid.
Figure 9:
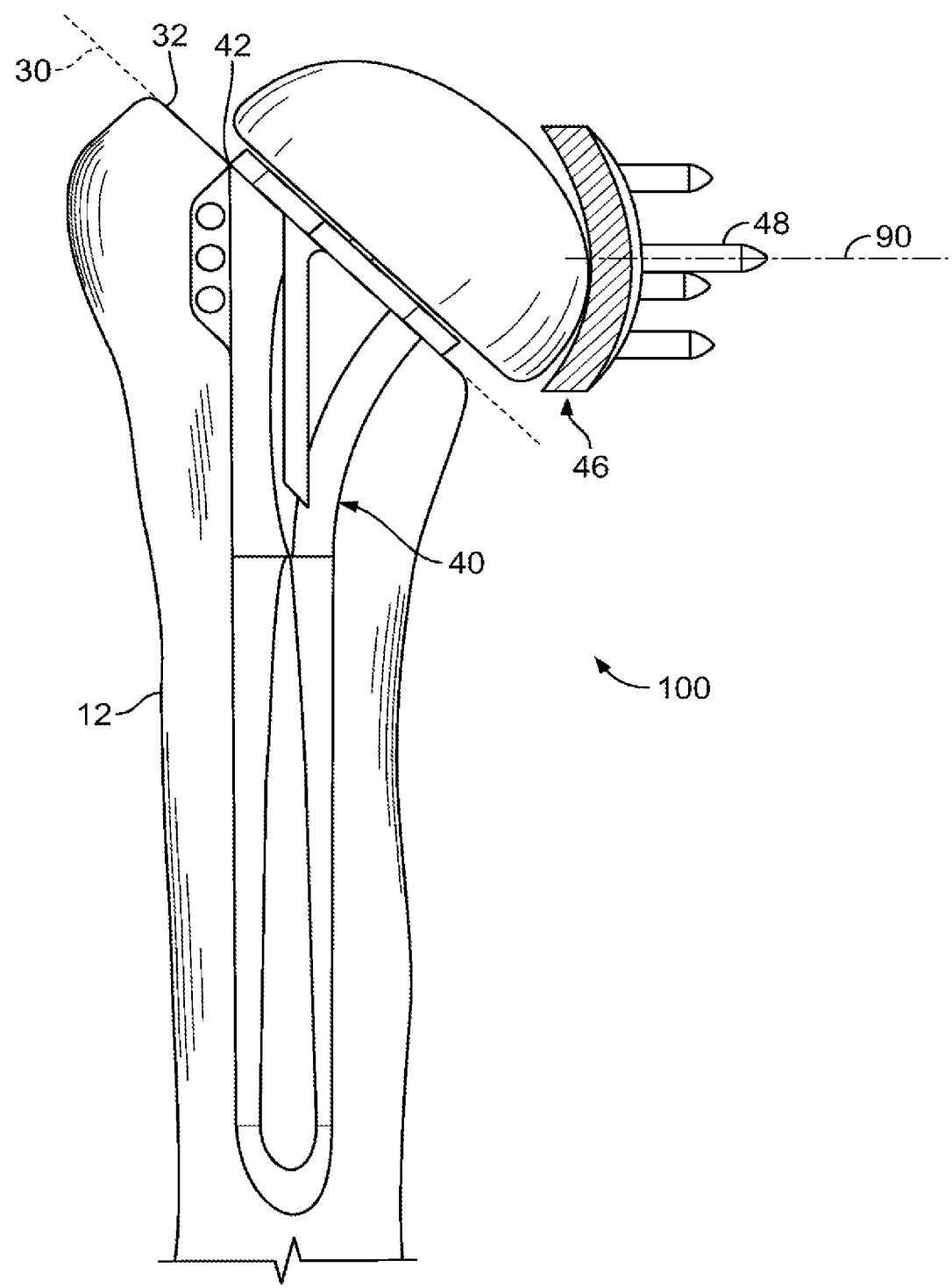
FIG. 9 is a view of a total shoulder arthroplasty prosthesis implant after a humerus and a glenoid of a patient has been resected to receive a humeral stem component and glenoid component, respectively.

Base portion 52 of guide 50 includes guide slot 68 for guiding the surgical instrument. Guide slot 68 is preferably located approximately 135° from a line perpendicular to a longitudinal axis of the humeral stem, also referred to as the neck-shaft angle that will be resected. The resected neck-shaft angle preferably matches the neck-shaft angle of the humeral stem component. The neck shaft angle may be greater or less than 135°, but preferably lies between a range of 110° and 160°. Guide slot 68 preferably produces a flat resection cut 32 as shown in FIG. 9 so that the version is dedicated. Humeral stem version is the positioning of the humeral stem in the correct position in the humeral canal when viewing from the top of humeral head 29 as shown in FIG. 5. Lateral side 23 of humeral head 29 is also shown in FIG. 5. If a stem is positioned with a trunion of the stem in the A-B direction, this would be 0° retroversion. A stem positioned in the A-C direction is at 30° of retroversion. Another way to find 30° of retroversion is to have the most lateral point on the stem position in line with point D which is 8-10 mm retroversion from the bicipital groove. Also, a recess is preferably reamed into shaft 17 of humerus 12 such that a humeral stem component can be implanted therein.

One method of making patient-specific cutting guide 50 for guiding a surgical instrument for resecting a portion of humerus 12, includes first obtaining image data associated with at least a portion of humerus 12 and generating a model of humerus 12 from the image data. Guide 50 preferably includes a base portion 52 including a contact surface shaped to substantially match an outer surface of a neck portion 13 of humerus 12, at least one proximal stabilization member 54 extending medially from base portion 52 and having a contact surface 56 shaped to substantially match an outer surface 11 of a head portion 14 of humerus 12, and at least one distal stabilization member 53 includes a contact surface shaped to substantially match an outer surface of a shaft portion 17 of humerus 12. The method further includes providing the guide 50 with a guide slot 68 for directing movement of the surgical instrument, wherein creating the contact surfaces of base portion 52, at least one proximal stabilization member 54, and at least one distal stabilization member 53 includes shaping the contact surfaces based on the model of the humerus 12 generated from the image data.

Figure 6A:
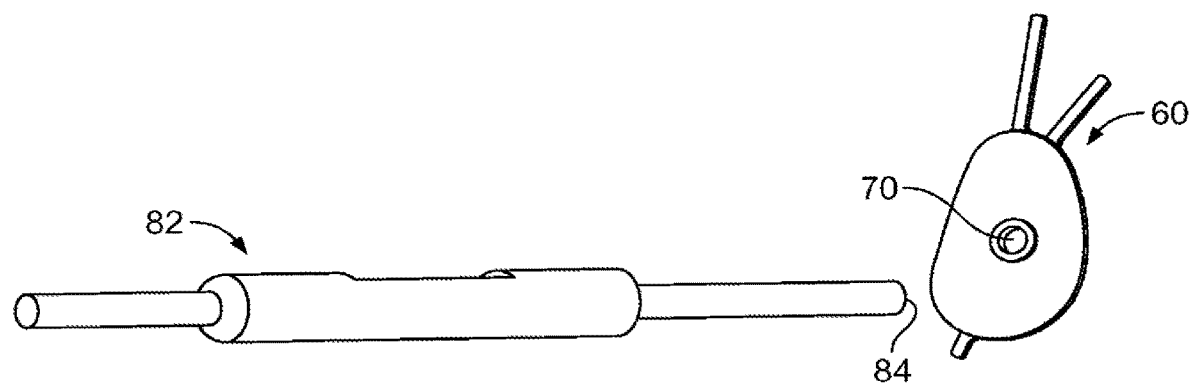
FIG. 6A is a view of an embodiment of a patient-specific cutting guide of the present invention for resecting the glenoid.
Figure 6B:
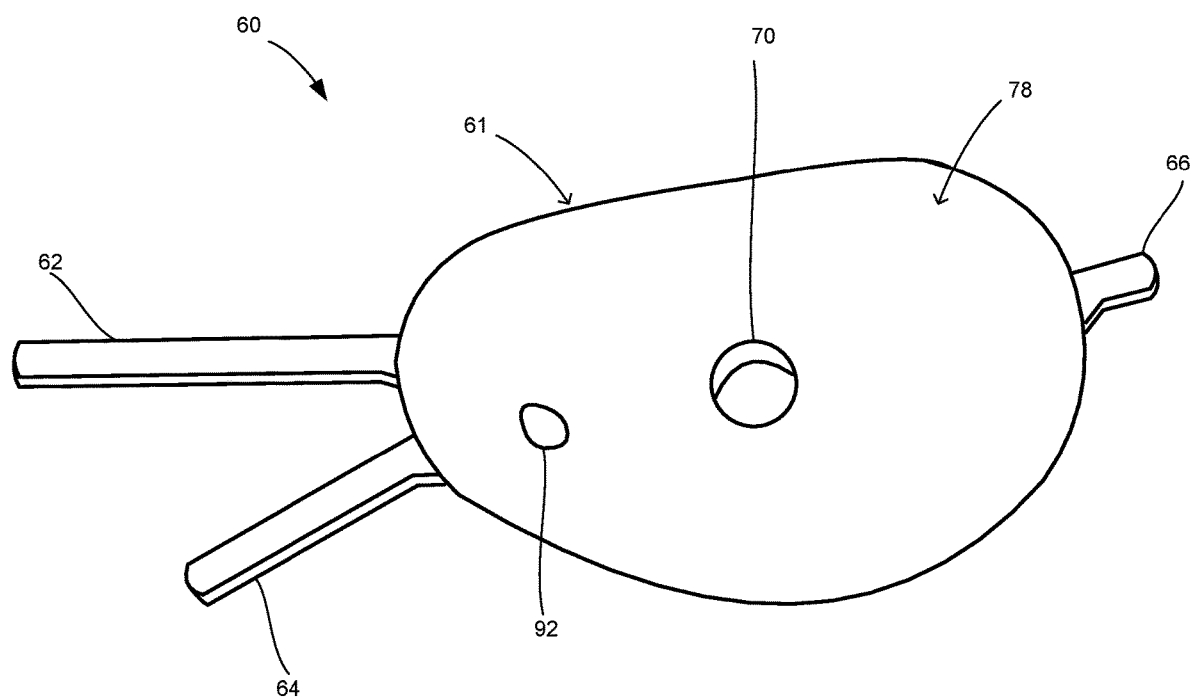
FIG. 6B is another view of the patient-specific cutting guide of FIG. 6A.
Figure 7:
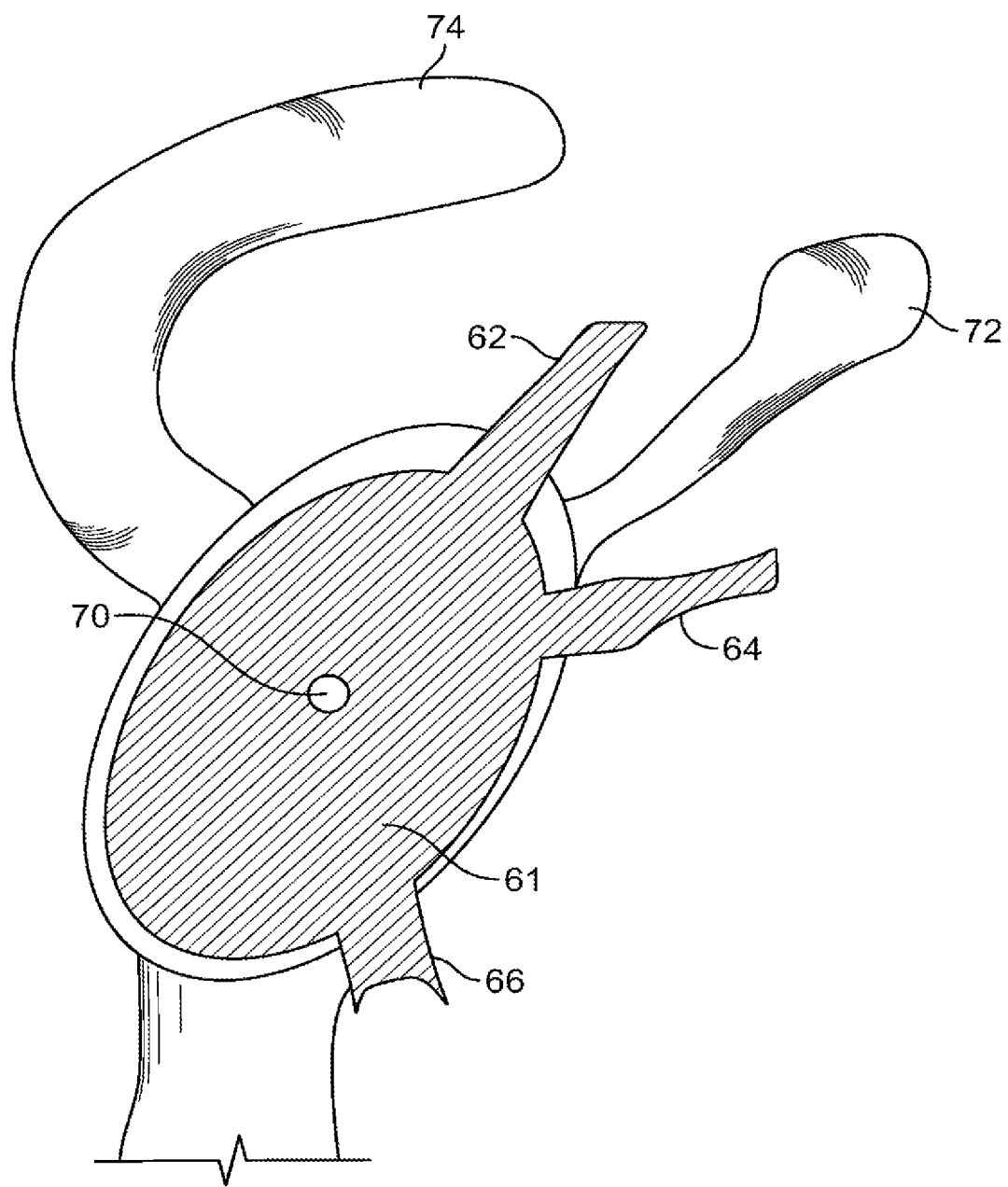
FIG. 7 is a view of the glenoid patient-specific cutting guide shown in FIGS. 6A and 6B received in a glenoid cavity of a patient.
Figure 8:
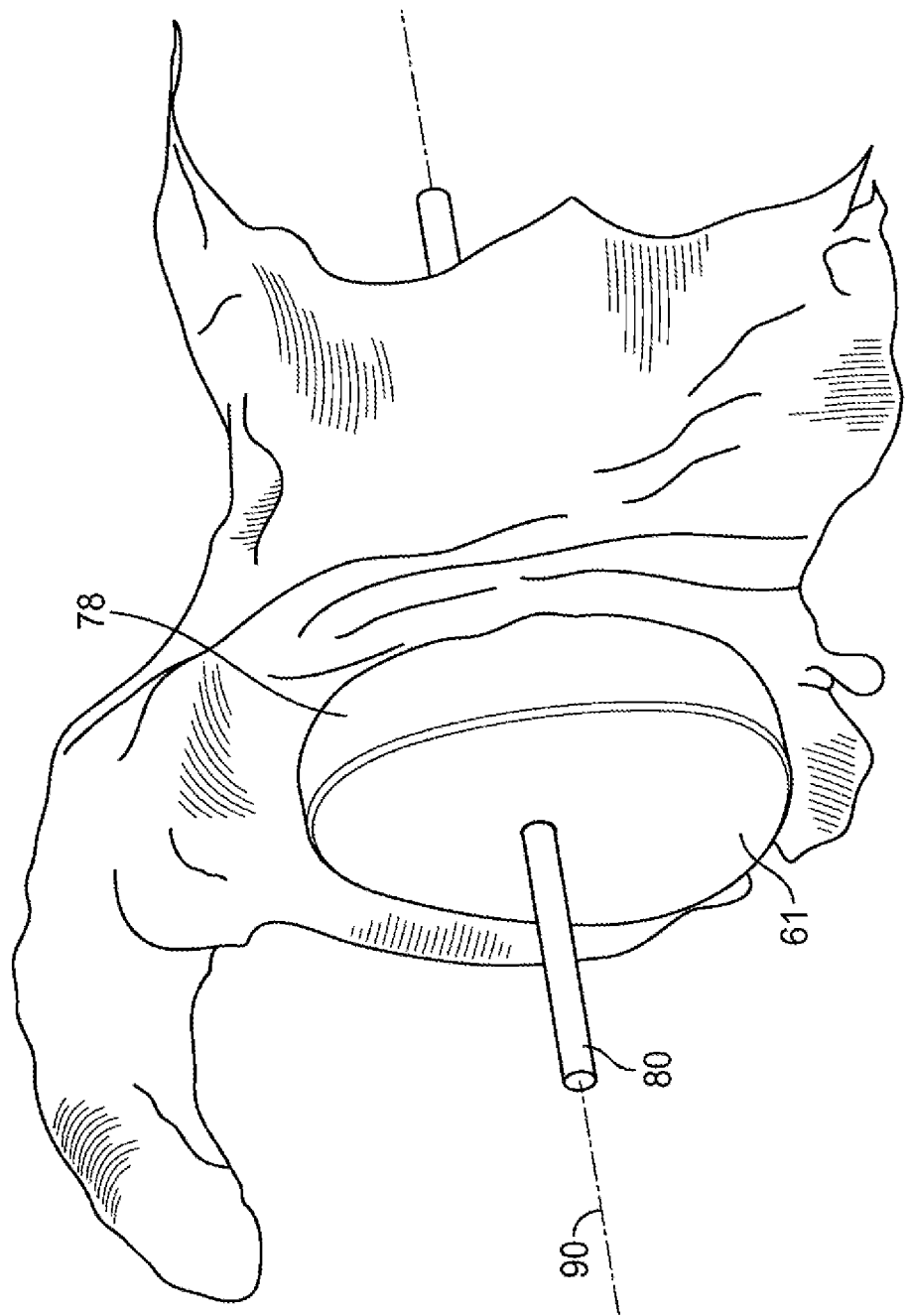
FIG. 8 is an alternate view of the cutting guide shown in FIGS. 6A and 6B received in the glenoid cavity of a patient.

FIGS. 6-8 show patient-specific cutting guide 60 for guiding a surgical instrument 82 for resecting a portion of glenoid 20 of a patient. Guide 60 includes a base portion 61 having a contact surface 78 shaped to substantially match at least a portion of a cavity 21 of glenoid 20. Base portion 61 includes a guide hole 70 extending therethrough. Guide hole 70 has an axis 90 coaxial with an axis of rotation. Guide pin 80 engages bone of cavity 21 after passing through guide hole 70 of base portion 61. Placement of guide pin 80 may be aided by surgical instrument 82 having a cannula 84. Guide hole 70 is preferably aligned with the centerline of the spine of the scapula such that guide pin 80 has the correct location and orientation once engaged to bone in cavity 21. Once guide pin 80 is correctly positioned, surgical instrument 82 and guide 60 are removed and guide pin 80 can be used to guide drilling of a guide recess (not shown) in cavity 21 used to accept a central screw or peg 48 protruding outwardly from a glenoid component 46 as shown in FIG. 9.

Guide 60 preferably includes stabilization members 62, 64, 66 extending outwardly from base portion 61 and having a contact surface shaped to substantially match an outer surface of a portion of a scapula 22 of the patient. Stabilization member 62 is preferably located right of the acromial process 74 and left of the coracoid process 72 and stabilization member 64 is preferably located right of the coracoid process 72 when guide 60 is correctly positioned in the cavity of the glenoid.

Contact surface 78 of base portion 61 preferably includes at least one shaped protrusion 92 configured to contact a unique anatomical feature in cavity 21 of glenoid 20 of the patient. In use, guide 60 can be rotated within cavity 21 of glenoid 20 until the at least one shaped protrusion 92 on contact surface 78 of base portion 61 keys into the unique anatomical feature in cavity 21 of glenoid 20.

One method of making patient-specific cutting guide 60 for guiding pin 80 used in guiding the resection of a portion of glenoid 20 includes obtaining image data associated with at least a portion of glenoid 20 and generating a model of glenoid 20 from the image data. Guide 60 preferably includes a base portion 61 with a contact surface 78 shaped to substantially match at least a portion of the glenoid cavity 21, the base portion 61 having a guide hole 70 extending therethrough, the guide hole 70 having an axis 90 coaxial with an axis of rotation. Guide 60 preferably further includes stabilization members 62, 64, 66 extending outwardly from base portion 61 each having a contact surface shaped to substantially match an outer surface of a portion of scapula 22. Contact surface 78 of base portion 61 and the contact surfaces of stabilization members 62, 64, 66 are created by shaping the contact surfaces based on the model of glenoid 20 generated from the image data.

After humerus 12 and glenoid 20 are resected, an example of a total shoulder arthroplasty prosthesis 100, as shown in FIG. 9, may be implanted. Humeral stem component 40 is preferably implanted into shaft 17 of humerus 12 with a bottom surface of flange 42 thereof lying adjacent flat resected surface 32 substantially co-axial with resection line 30. Glenoid component 46 is implanted into cavity 21 of glenoid 20 with central screw or peg 48 passing through an aperture in component 46 and into a guide recess created by the surgical instrument 80 being guided through guide hole 70 of guide 60.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patient-specific cutting guide for guiding a surgical instrument for resecting a portion of a glenoid of a patient comprising:

a base portion having a bone contacting surface with a shape configured to substantially match at least a portion of a cavity of the glenoid, the base portion having a guide hole at a first location extending therethrough and a circumferential edge between the bone contacting surface and a non-bone contacting planar surface, the bone contacting surface extending from the circumferential edge to the guide hole, the guide hole having an axis coaxial with an axis of rotation, the bone contacting surface of the base portion includes at least one shaped protrusion defining a nub protruding outwardly from the bone contacting surface at a second location different than the first location, the nub is spaced apart from the guide hole on the bone contacting surface and configured to key into an anatomical feature in the cavity of the glenoid to cause the patient-specific cutting guide to resist rotation about the axis of rotation within the cavity;

a first stabilization member extending outwardly from the base portion and having a contact surface with a second shape configured to substantially match an outer surface of a portion of a scapula of the patient and configured to be located left of a coracoid process when the cutting guide is positioned in the cavity of the glenoid, wherein the guide hole of the base portion is for guiding the surgical instrument to create a guide hole in the glenoid.

2. The patient-specific cutting guide of claim 1, further comprising a second stabilization member extending outwardly from the base portion and having a contact surface with a third shape configured to substantially match the outer surface of a portion of the scapula of the patient.

3. The patient-specific cutting guide of claim 2, wherein the second stabilization member is configured to be located right of the coracoid process when the cutting guide is positioned in the cavity of the glenoid such that the coracoid process is located between first and second stabilization members.

4. The patient-specific cutting guide of claim 1, further comprising second and third stabilization members each extending outwardly from the base portion and each having a contact surface with respective fourth and fifth shapes configured to substantially match the outer surface of a portion of the scapula of the patient.

5. The patient-specific cutting guide of claim 4, wherein the coracoid process is located between the first and second stabilization members.

6. The patient-specific cutting guide of claim 5, wherein the first and second stabilization members extend distally from the base portion and the third stabilization member extends proximally from the base portion.

7. The patient-specific cutting guide of claim 1, wherein the nub can be used to orient the cutting guide in a pre-operatively planned position.

8. The patient-specific cutting guide of claim 1, wherein the base portion includes a circumferential rim, the at least one stabilization member being an elongated member extending outwardly from the circumferential rim.

9. A patient-specific cutting guide for guiding a surgical instrument for resecting a portion of a glenoid of a patient comprising:

a base portion having an outer surface, a bone contacting surface, a guide hole at a first location extending through the outer and contact surfaces, a circumferential edge between the bone contacting surface and a non-bone contacting planar surface, and at least one shaped protrusion defining a nub protruding outwardly from the bone contacting surface at a second location different than the first location, the bone contacting surface extending from the circumferential edge to the guide hole with a shape configured to substantially match at least a portion of a cavity of the glenoid, the guide hole having an axis coaxial with an axis of rotation, the nub being spaced apart from the guide hole on the bone contacting surface and configured to key into an anatomical feature in the cavity of the glenoid to cause the patient-specific cutting guide to resist rotation about the axis of rotation within the cavity; and a first stabilization member extending outwardly from the base portion and having a contact surface with a second shape configured to substantially match an outer surface of a portion of a scapula of the patient, wherein the guide hole of the base portion is for guiding the surgical instrument to create a guide hole in the glenoid.

10. The patient-specific cutting guide of claim 9, further comprising a second stabilization member extending outwardly from the base portion and having a contact surface with a third shape configured to substantially match the outer surface of a portion of the scapula of the patient.

11. The patient-specific cutting guide of claim 10, wherein the first stabilization member is configured to be located left of a coracoid process when the cutting guide is positioned in the cavity of the glenoid.

12. The patient-specific cutting guide of claim 11, wherein the second stabilization member is configured to be located right of the coracoid process when the cutting guide is positioned in the cavity of the glenoid such that the coracoid process is located between first and second stabilization members.

13. The patient-specific cutting guide of claim 9, further comprising second and third stabilization members each extending outwardly from the base portion and each having a contact surface with respective fourth and fifth shapes configured to substantially match the outer surface of a portion of the scapula of the patient.

14. The patient-specific cutting guide of claim 13, wherein a coracoid process is located between the first and second stabilization members.

15. The patient-specific cutting guide of claim 14, wherein the first and second stabilization member extend distally from the base portion and the third stabilization member extends proximally from the base portion.

16. The patient-specific cutting guide of claim 9, wherein the nub can be used to orient the cutting guide in a pre-operatively planned position.

17. The patient-specific cutting guide of claim 9, wherein the base portion includes a circumferential rim, the at least one stabilization member being an elongated member extending outwardly from the circumferential rim.

18. A patient-specific cutting guide for guiding a surgical instrument for resecting a portion of a glenoid of a patient comprising:

a base portion having a convex bone contacting surface, a guide hole at a first location extending through the base portion, a circumferential edge defined by the intersection of bone contacting surface and a non-bone contacting planar surface, and at least one shaped protrusion defining a nub protruding outwardly from the bone contacting surface at a second location different than the first location, the nub is spaced apart from the guide hole on the bone contacting surface;

a first stabilization member extending outwardly from the base portion and having a first contact surface configured to substantially match an outer surface of a portion of a scapula of the patient, the first stabilization member being a first length;
a second stabilization member extending outwardly from the base portion and having a second contact surface configured to substantially match the outer surface of a portion of the scapula, the second stabilization member being a second length; and
a third stabilization member extending outwardly from the base portion and having a third contact surface configured to substantially match the outer surface of a portion of the scapula, the third stabilization member being a third length,
wherein the first, second, and third contact surfaces are created based on a patient-specific model of the glenoid,
wherein the first, second, and third lengths are each a different length, and
wherein the guide hole of the base portion is for guiding the surgical instrument to create a guide hole in the glenoid.

\* \* \* \* \*